United States Patent [19]
Tremaine et al.

[11] Patent Number: 6,156,004
[45] Date of Patent: Dec. 5, 2000

[54] SUCTION AND IRRIGATION HANDPIECE AND TIP WITH RETRACTABLE SPLASH SHIELD

[75] Inventors: Laurence W. Tremaine, West Warwick; Robert Sakal, Riverside, both of R.I.; Stephen Albrecht, South Walpole, Mass.

[73] Assignee: C. R. Bard, Inc., Murray Hill, N.J.

[21] Appl. No.: 08/667,957

[22] Filed: Jun. 18, 1996

[51] Int. Cl.[7] ................................................ A61M 1/00
[52] U.S. Cl. ............................................. 604/27; 604/43
[58] Field of Search ................................. 604/27, 35, 39, 604/40, 42, 43, 118, 119

[56] References Cited

U.S. PATENT DOCUMENTS

| | | |
|---|---|---|
| 517,274 | 3/1894 | Gullings . |
| 906,711 | 12/1908 | Hill et al. . |
| 1,178,898 | 4/1916 | Young . |
| 1,602,215 | 4/1926 | Smith . |
| 3,952,743 | 4/1976 | Harrison . |
| 4,294,251 | 10/1981 | Greenwald et al. . |
| 4,301,798 | 11/1981 | Anderson . |
| 4,465,479 | 8/1984 | Meisch . |
| 4,493,694 | 1/1985 | Wuchinich . |
| 4,553,957 | 11/1985 | Williams et al. . |
| 4,573,979 | 3/1986 | Blake . |
| 4,652,255 | 3/1987 | Martinez . |
| 4,692,140 | 9/1987 | Olson . |
| 4,769,003 | 9/1988 | Stamler ...................................... 604/39 |
| 4,935,006 | 6/1990 | Hasson ...................................... 604/43 |
| 5,024,615 | 6/1991 | Büchel . |
| 5,460,604 | 10/1995 | Arnett et al. . |
| 5,464,390 | 11/1995 | Arnett et al. . |
| 5,496,290 | 3/1996 | Ackerman ............................... 604/268 |
| 5,554,111 | 9/1996 | Morrey et al. ............................ 604/26 |

FOREIGN PATENT DOCUMENTS

WO 8201824   6/1982   WIPO .

OTHER PUBLICATIONS

Loehne, Harriett Baugh, "Chapter 17–Pulsatile Lavage with Concurrent Suction", Wound Care—A Collaborative Practice Manual for Physical Therapists and Nurses, Aspen Publishers, Inc., pp. 389–398.

Primary Examiner—Wynn Wood Coggins
Attorney, Agent, or Firm—Arthur Z. Bookstein; John F. Perullo

[57] ABSTRACT

An apparatus for irrigating a local irrigation site includes a suction/irrigation tip that is removably connected to a suction/irrigation handpiece. The tip has an irrigation tube for directing irrigation liquid to the irrigation site, and a suction tube coaxially aligned within the irrigation tube. The handpiece pumps irrigation liquid from an external reservoir, through the annular space between the irrigation tubes and the suction tube to the irrigation site. Suction is applied to the site through the central suction lumen which has a large unobstructed opening to reduce clogging. A flexible splash shield, slidably mounted to the tip, is conically shaped and extends distally from a collar to a rim. The rim is sized to fit around and about the local site.

24 Claims, 4 Drawing Sheets

ND TIP WITH RETRACTABLE SPLASH
SUCTION AND IRRIGATION HANDPIECE AND TIP WITH RETRACTABLE SPLASH SHIELD

FIELD OF THE INVENTION

This invention relates generally to medical irrigation systems and, more particularly, to hand-held medical irrigation devices that use suction/irrigation tips.

BACKGROUND OF THE INVENTION

Suction/irrigation tips with splash shields commonly are attached to the front (distal) end of hand-held suction irrigation handpieces when localized irrigation is needed. The splash shield typically is a conical member having a distal rim that is intended to be pressed against and about the body region where the localized irrigation is desired. Such devices are commonly used, for example, in wound management environments to irrigate bed sores or other externally exposed traumatized regions of a patient's body. These devices also are commonly used in orthopedic surgical environments to clean out joints during orthopedic surgery. During orthopedic uses, however, the shield generally is removed from the distal end of the tip so that the tip may be inserted directly into the joint being treated.

U.S. Pat. No. 4,692,140 (Olson) shows a typical tip that may be used with an irrigation handpiece. The Olson tip has an outer (suction) tube, an inner (irrigation) tube coaxially aligned within the suction tube, and a web (referred to as "pegs" in Olson) that support the distal end of the irrigation tube within the suction tube. The annular space between the tubes provides a suction pathway for biological debris aspirated from the irrigation site. Aspirated biological debris is directed by the tip suction pathway into a handpiece suction lumen, from which it flows through a connecting tube to a debris collection chamber. The tip suction pathway appears to clog easily, however, because it has a relatively small cross-sectional dimension. The web also obstructs debris from being drawn into the suction pathway since it partially covers the open distal end of the pathway. If the suction pathway becomes clogged, the irrigation or surgical procedure must be suspended and the suction pathway must either be cleaned out, or a new tip must be attached to the end of the suction irrigator. These additional steps are inefficient and inconvenient to both the attendant and patient.

The Olson tip also has a flexible, conical splash shield permanently fastened to the distal end of the tip. In addition to confining irrigation fluid to a local site, the shield undesirably prevents the irrigation outlet orifice and the suction orifice from physically contacting the surface being irrigated. This is so because the shield extends distally a certain distance from the distal end of the suction tube. In many instances, however, the physician or attendant may need to adjust this distance, for example, to bring the irrigation outlet orifice directly against the wound to increase the impact of the emitted irrigation fluid. In other instances, such as in an orthopedic surgical environmental, it often is desirable to extend the suction/irrigation tip deeply into a wound or a joint to more effectively clean that region. The permanently fastened Olson shield does not readily permit variation in the distance between the distal end of the tip and the site and thus, inhibits such close contact irrigation. One approach suggested by Olson to remedy this problem is to provide visual rings about the flexible splash shield to facilitate cutting the splash shield to a smaller size. In addition to being both time consuming and cumbersome, the structure of the tip is permanently altered. A new tip must be attached to the handpiece if use of a splash shield subsequently becomes necessary.

It is therefore among the general objects of the invention to provide an improved suction/irrigation tip that remains substantially clog free, and has a splash shield that easily enables close contact with an irrigation site when necessary.

SUMMARY OF THE INVENTION

In accordance with one aspect of the invention, the suction tube in a detachable suction and irrigation tip is concentrically aligned within an outer irrigation tube. Irrigation liquid is directed to the irrigation site through the annular space between the inner and outer tubes, but suction occurs through the inner lumen. The tip is less subject to clogging than tips in which the suction occurs through the annular space because the largest linear dimension of the suction lumen is larger than the linear dimension of the annular irrigation lumen. The tip also has a connector that is connectable to a fitting in the handpiece that fluidly communicates the tip irrigation lumen with the handpiece irrigation lumen, and the tip suction lumen with the handpiece suction lumen.

In accordance with another aspect of the invention, the tip also includes a flexible splash shield that is slidably mounted on the outer tube to confine irrigation liquid to a local irrigation site. When necessary, the splash shield may be retracted so that the distal end of the tip may be positioned directly against an irrigation site. The splash shield includes a proximal collar and a conical body that diverges in a distal direction to a distal rim. The distal rim is sized to fit around and about the irrigation site.

It is among the objects of the invention to provide a suction and irrigation apparatus having a reduced risk of clogging with aspirated biological debris.

It is another object of the invention to provide a suction and irrigation tip having a splash shield that is slidable on the tip and moldable to the shape of a local irrigation site.

BRIEF DESCRIPTION OF THE DRAWINGS

The foregoing and other objects and advantages of the invention will be appreciated more fully from the following further description thereof with reference to the accompanying drawings wherein.

DESCRIPTION OF THE ILLUSTRATIVE EMBODIMENT

Figures 1, 2:
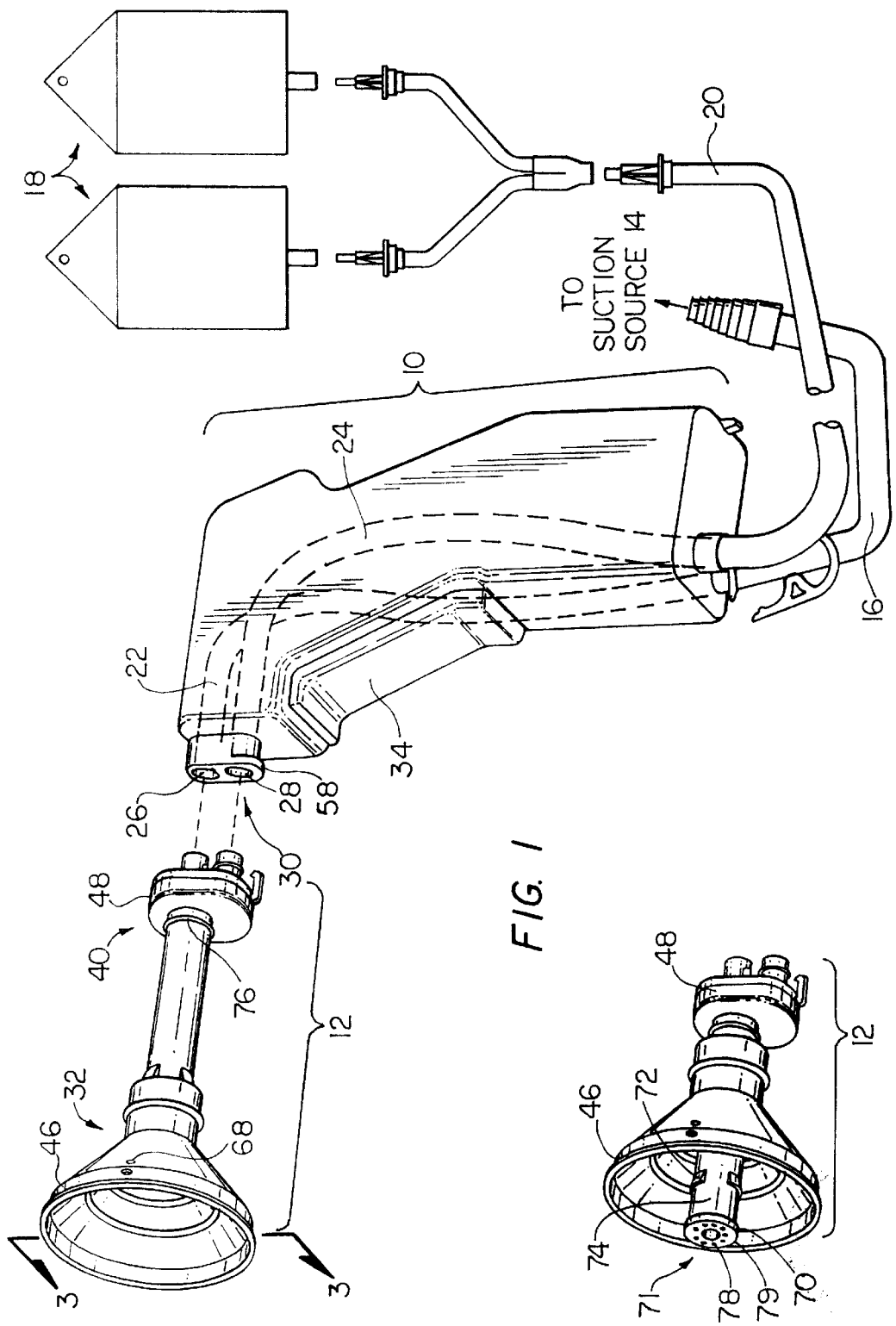
FIG. 1 is a perspective view of the irrigation system in accordance with the invention.
FIG. 2 is a perspective view of the suction irrigation tip with the splash shield retracted.

FIG. 1 illustrates the main components of the suction irrigation system, which includes a conventional suction irrigation handpiece 10 and a suction irrigation tip 12 that is detachably connectable to the handpiece 10. The handpiece 10 is connected to a suction source 14 (e.g., wall suction) through flexible suction tubing 16, and to an irrigation source 18 (e.g, a saline bag) through flexible irrigation tubing 20. Irrigation fluid is pumped through the handpiece 10 and tip 12, to the irrigation site. Spent irrigation fluid and biological debris are aspirated through the tip 12 and handpiece 10, to a debris container (not shown).

The handpiece 10 may be a Simpulse Solo™ suction irrigator (available from C.R. Bard, Inc. of Murray Hill, N.J.) which has a self contained pump, battery, and motor (omitted for clarity), described in more detail in co-pending U.S. patent application No. 08/389,155 (assigned to C.R. Bard, Inc.). A suction lumen 22 and an irrigation lumen 24, both shown in phantom, extend through the entire length of the handpiece 10. The suction lumen 22 is connectable to a suction source 14 at a first end and terminates at a suction port 26 at a second end. Similarly, the irrigation lumen 24 is connectable to an irrigation source 18 at the first end and terminates at an irrigation port 28 at the second end. Both ports 26 and 28 are formed in a fitting 30 at the distal end of the handpiece 10. When the tip 12 is connected to the handpiece 10 and the handpiece 10 is energized, irrigation fluid passes through the irrigation port 28 and into the tip 12. The irrigation fluid is emitted in a pulsatile liquid stream from the distal end 32 of the tip 12 at a pulsating frequency that is controllable by a handpiece trigger 34. Suction also is applied to the site through the handpiece 10 and tip 12.

Figure 3:
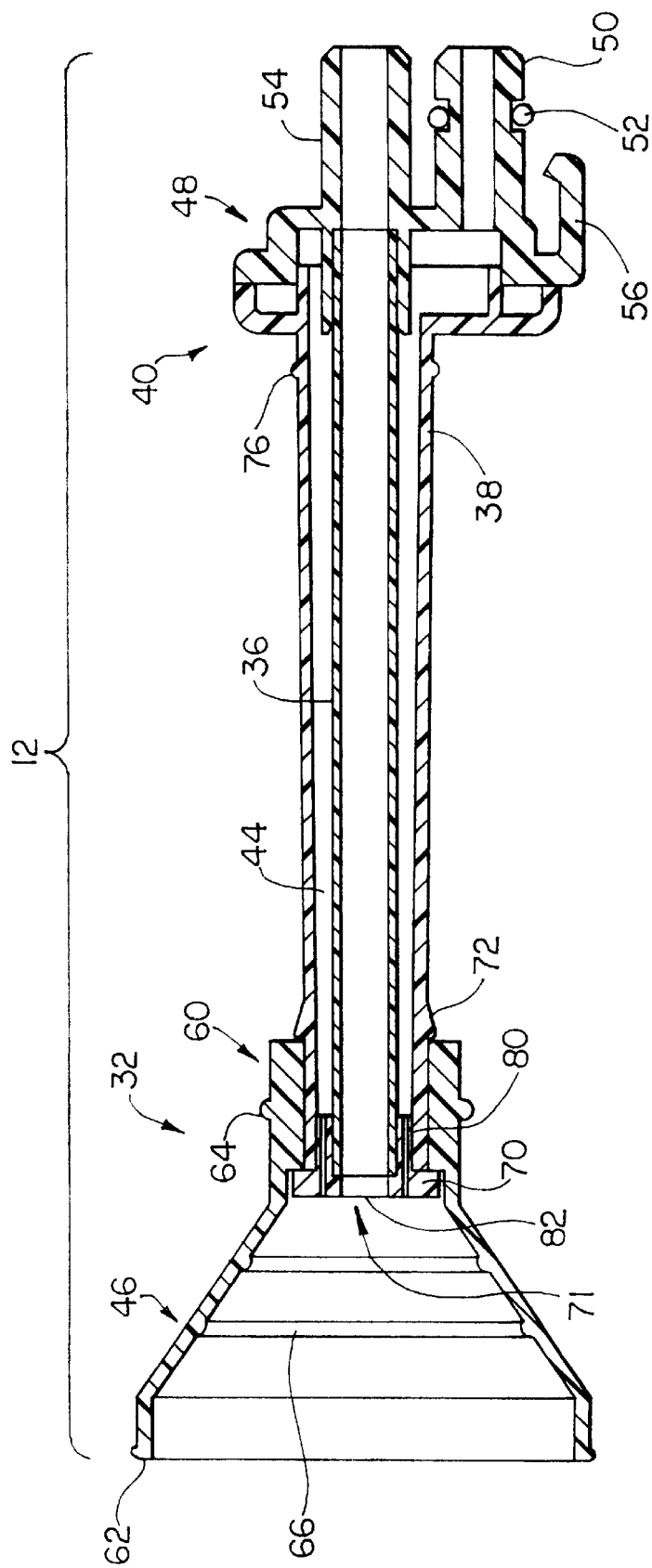
FIG. 3 is a longitudinal cross section of the suction irrigation tip along line 3—3 of FIG. 1.

The tip 12, illustrated in cross section in FIG. 3, may be made from a hard, substantially transparent plastic. The tip 12 includes an inner (suction) tube 36 coaxially disposed entirely within an outer (irrigation) tube 38, a flexible splash shield 46 and a connector 48. The suction tube 36 defines a substantially straight flow path from the proximal end 40 of the tip 12 to the distal end 32 of the tip 12, and the annular space 44 between the suction and irrigation tubes 36 and 38 provides a pathway for irrigation fluid. The splash shield 46, slidably mounted to the irrigation tube 38. enables treatment to be confined to a localized treatment site. The connector 48 at the proximal end 40 of the tip 12 detachably connects the tip 12 to the handpiece 10.

When the tip 12 is connected to the handpiece 10, an irrigation connector 50, extending proximally from the tip connector 48, fluidly connects the tip annular (irrigation) space 44 to the handpiece irrigation port 28. A sealing O-ring 52 may encircle the irrigation connector 50 to fluidly seal that connection. Irrigation fluid therefore first passes through the flexible irrigation tubing 20 to the handpiece irrigation lumen 24. The fluid then passes through the irrigation connector 50, to the annular space 44 and is emitted at the distal end 32 of the tip 12.

Similarly, a suction connector 54, extending proximally from the tip connector 48, fluidly connects the tip suction tube 36 with the handpiece suction port 26. The suction connector 54 and suction tube 36 together form a substantially straight flow path for aspirated debris from the distal end 32 of the tip 12 to the handpiece suction port 26. Aspirated debris from the site therefore first passes straight through the suction tube 36, then through the suction port 26 to the handpiece suction lumen 22, and then through the flexible suction tubing 16 to the debris container.

A clip 56 extending proximally from the connector 48 removably secures the tip 12 to the handpiece 10 by coupling with a lip 58 formed along the underside of the handpiece fitting 30. Accordingly, the tip 12 is removably connected, by a friction fit, to the handpiece 10 by the combination of the clip 56, the suction connector 54, and the irrigation connector 50. The tip 12 may be easily attached to and removed from the handpiece 10 with a minimum amount of force.

The flexible shield 46 includes a proximal collar 60 and a conical body that diverges in a distal direction to a distal rim 62. The collar 60 is slidably mounted to the irrigation tube 38 and has an annular gripping ridge 64 to facilitate gripping the collar 60. A plurality of circumferential ridges 66 (e.g., three) are included on the inner surface of the shield 46 to serve as cutting guides for cutting the shield 46. Vent holes 68 formed in the side of the shield 46 prevent the shield 46 from collapsing under suction and also enable air to mix with the debris aspirated from the site to avoid stagnation of debris within the shield. The shield 46 may be made from a flexible, substantially clear plastic that may be shaped during use to conform to the shape and contour of the irrigation site.

The collar 60 may be secured to the distal end 32 of the tip 12 by both an annular flange 70 extending radially from a shower head nozzle 71 (shown in FIGS. 2 and 3), and a discontinuous circumferential ridge 72 circumscribing the outer surface of the irrigation tube 38. The securing ridge 72 has two discontinuities 74 that enable the shield 46 to be more easily forced over the securing ridge 72. The shield 46 may be retracted proximally (FIG. 2), over the securing ridge 72, by applying a proximal force to either the rim 62 or the gripping ridge 64 on the collar 60. The irrigation tube 38 may be tapered slightly toward the distal end 32 of the tip 12 to increase the resistance to proximally retracting the shield 46. A stop ridge 76 may circumscribe the proximal end of the irrigation tube 38 to prevent the splash shield 46 from being retracted into contact with the connector 48.

Figure 4:
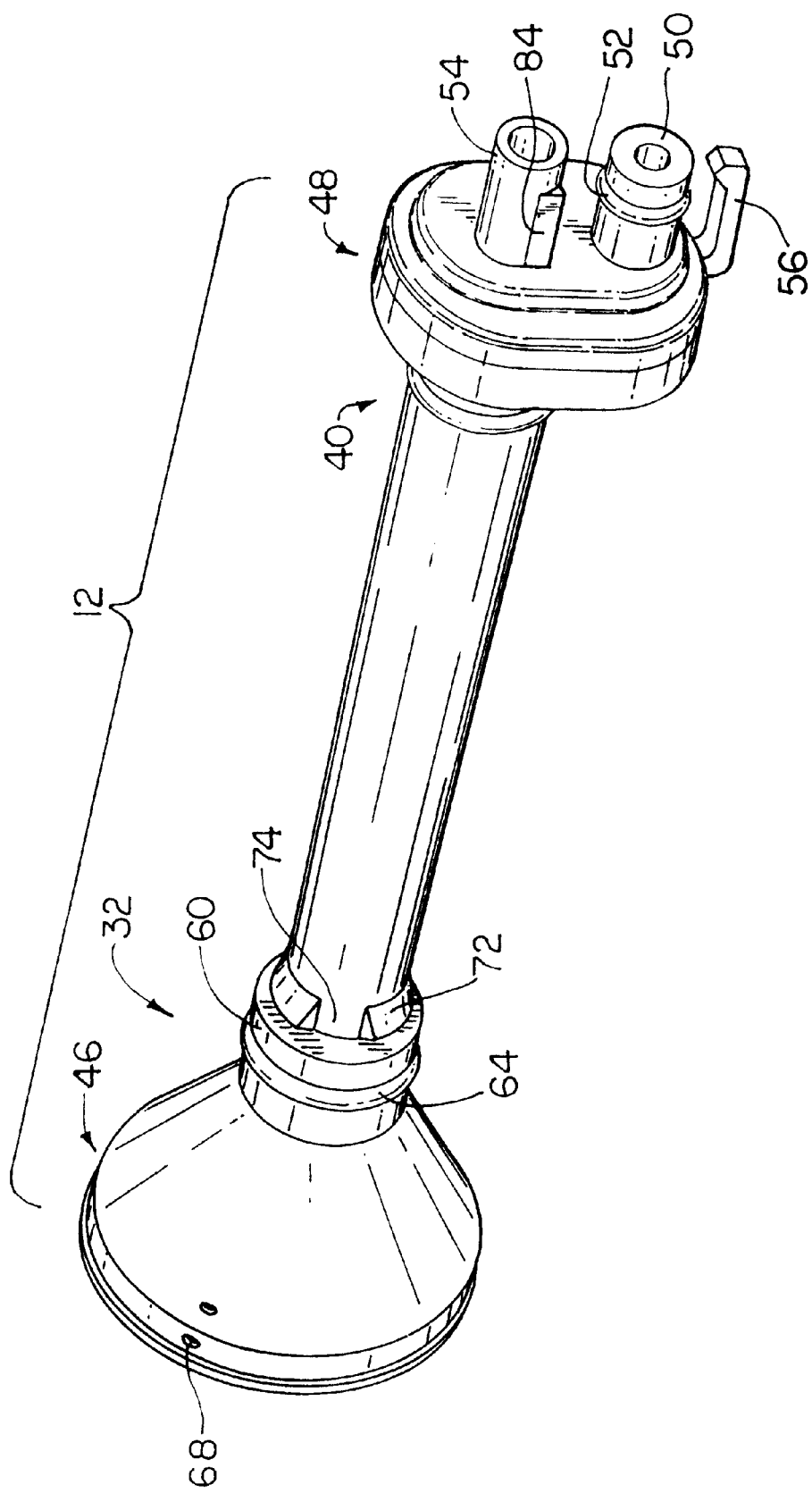
FIG. 4 is a perspective view of the suction irrigation tip showing the rear and side portions of the tip.
Figure 5:
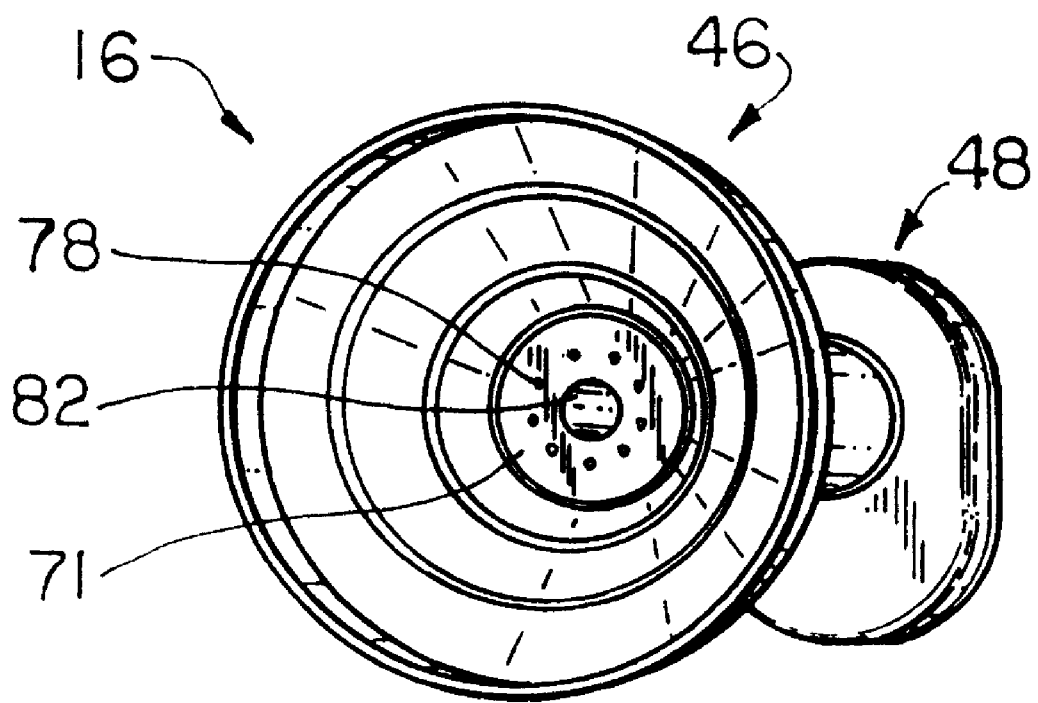
FIG. 5 is a front perspective view of the suction irrigation tip.

The shower head nozzle 71, fastened to the distal end 32 of the tip 12 and including an end wall 79 and a cylindrical wall extending from the end wall 80, serves a number of important functions. Primarily, as discussed above, it partially secures the splash shield 46 to the tip 12. In addition, it can be configured to emit irrigation fluid from the tip 12 in a specialized spray pattern. To that end, as shown in FIG. 4, the shower head nozzle 71 has a plurality of irrigation holes 78 (e.g., nine) longitudinally formed through the cylindrical wall 80 and end wall 79, and a central suction hole 82. The diameter of the central suction hole 82 should have approximately the same diameter as the inner diameter of the suction tube 36 such as, for example, 0.1875 inches. The number, shape, and size of the irrigation holes 78 are selected to provide a specialized spray pattern for the irrigation fluid and to regulate the force with which the irrigation fluid is emitted from the tip 12. Accordingly, the suction/irrigation tip 12 may be customized to be usable with certain pumps only. For example, when irrigating a wound on a patient's skin (e.g., a bed sore), it is preferred that the irrigation fluid be emitted from the tip 12 at a force not exceeding 15 p.s.i. When the tip 12 is used with the Simpulse Solo™ suction irrigator, nine holes 78 having a diameter of 0.040 inches have produced satisfactory results. Similarly, when used with the Simpulse Plus™ suction irrigator, available from C.R. Bard, Inc., four holes 78 having a diameter of 0.040 inches have produced satisfactory results.

During the irrigation procedure, it therefore is important that the attendant easily select the tip 12 that corresponds with a specific handpiece. Accordingly, it is preferred that the tip 12 have a simple identification means that quickly and easily indicates the tip 12 that corresponds to the pump being used. To that end, the tip connector 48 may be color coded to correlate with the handpiece 10. For example, the tip connector 48 to be used with the Simpulse Solo™ may be colored purple, while the tip connector 48 to be used with the Simpulse Plus™ may be colored green. Furthermore, the tip connector 48 may be shaped to fit into the fitting 30 of the correct pump only. In so doing, the wrong tip 12 cannot fit into the wrong pump. To that end, either the irrigation connector 50 or the suction connector 54 may be provided with a ridge 84 or other irregularity, and the corresponding irrigation port 28 or suction port 26 may be molded to that complimentary shape. The connector 48 may only be connected to the corresponding port for a fluid tight fit.

Another important function provided by the shower head nozzle 71 is to coaxially secure the distal end of the suction tube 36 within the irrigation tube 38. To that end, the proximally depending cylindrical wall 80 may have an outer diameter (e.g., 0.375 inches) that is sized to be fastened to the inner surface of the irrigation tube 38. During manufacture, the outer surface of the cylindrical wall 80 is bonded to the inner surface of the irrigation tube 38. Similarly, the inner diameter of the cylindrical wall 80 may be sized to be fastened to the outer surface of the suction tube 36. During manufacture, the inner surface of the cylindrical wall 80 is bonded to the outer surface of the suction tube 36.

When used to irrigate an externally traumatized region of the body (e.g., bed sores), the tip 12 is connected to the handpiece 10, the flexible suction tubing 16 is connected to the handpiece suction lumen 22, and the flexible irrigation tubing 20 is connected to the handpiece irrigation lumen 24. The shield 46 may be positioned at the distal end 32 of the tip 12 and the rim 62 may be positioned at the local irrigation site. The attendant may then simultaneously irrigate and aspirate the site by depressing the handpiece trigger 34. The attendant may retract the shield 46 to put the shower head nozzle 71 directly against, or in very close proximity to, the irrigated site. After retracting the shield 46, it may be returned to the distal end 32 of the tip 12 for further localizect irrigation. The relatively large cross-sectional area of the suction tube 36 reduces the possibility of clogging. After use, the tip 12 and handpiece 10 are discarded.

When used to irrigate a joint during orthopedic surgery, the tip 12, flexible suction tubing 16, and flexible irrigation tubing 20 are all connected to the handpiece 10 as previously described. The shield 46 may be retracted entirely to the stop ridge 76 so that the suction and irrigation tubes 36 and 38 may be directly inserted into the joint being treated. Again, the relatively large diameter of the suction tube 36 reduces the possibility of clogging with bone fragments and other biological debris. After use, the tip 12 and handpiece 10 are discarded.

It should be understood that the foregoing description of the invention is intended merely to be illustrative thereof and that other modifications and embodiments may be apparent to those skilled in the art without departing from its spirit.

Having thus described the invention, what we desire to claim and secure by Letters Patent is:

1. An apparatus for irrigating an irrigation site comprising:
    a handpiece defining a suction lumen and an irrigation lumen; and
    a detachable tip having a proximal end and a distal end, the tip further comprising:
        an irrigation tube;
        a suction tube substantially coaxially disposed entirely within the
        irrigation tube; and
        a connector for connecting the tip to the handpiece.

2. The apparatus as defined by claim 1 wherein the suction tube defines a substantially straight suction flow path from the distal end of the tip to the proximal end of the tip.

3. The apparatus as defined by claim 1 wherein the tip further includes a flexible splash shield slidably mounted on the irrigation tube.

4. The apparatus as defined by claim 3 wherein the splash shield is conically shaped and extends distally from a collar to a rim.

5. The apparatus as defined by claim 1 wherein the connector has a suction connector for fluidly connecting the suction tube to the handpiece suction lumen, the suction connector and suction tube together forming a substantially straight flow path from the distal end of the tip to the handpiece suction lumen.

6. An apparatus for irrigating an irrigation site comprising:
    a handpiece defining a suction lumen and an irrigation lumen; and
    a tip having a proximal end and a distal end and further comprising:
        an irrigation tube having proximal and distal ends;
        a connector for removably connecting the irrigation tube to the handpiece; and
        a flexible splash shield slidably mounted to the irrigation tube and having a first position on the tube in which it surrounds at least a portion of the distal end of the irrigation tube and a second position on the tube in which it is proximal to the distal end of the irrigation tube leaving the distal end of the tube uncovered.

7. The apparatus as defined by claim 6 further including a suction tube substantially coaxially disposed entirely within the irrigation tube.

8. The apparatus as defined by claim 7 wherein the connector has a suction connector for fluidly connecting the suction tube to the handpiece suction lumen, the suction connector and suction tube together forming a substantially straight flow path from the distal end of the tip to the handpiece suction lumen.

9. The apparatus as defined by claim 6 wherein the splash shield is conically shaped and extends distally from a collar to a rim.

10. A detachable suction and irrigation tip for use with a handpiece having a suction lumen, the tip having a proximal end and a distal end and further comprising:
    an irrigation tube having a distal end and an emission aperture at its distal end through which liquid can be directed to an external irrigation site; and
    a suction tube substantially coaxially disposed entirely within the irrigation tube, an irrigation lumen defined between the suction and irrigation tubes, the suction tube defining a substantially straight flow path from the proximal end of the tip to the distal end of the tip.

11. The tip as defined by claim 10 further including a connector for detachably connecting the tip to the handpiece.

12. The tip as defined by claim 11 wherein the connector has a suction connector for fluidly connecting the suction tube to the handpiece suction lumen, the suction connector and suction tube together forming a substantially straight flow path from the distal end of the tip to the handpiece suction lumen.

13. The tip as defined by claim 10 further including a flexible splash shield slidably mounted to the irrigation tube.

14. A suction and irrigation tip for use with a handpiece, the tip having a proximal end and a distal end and further comprising:
    an irrigation tube having proximal and distal ends;

a connector for detachably connecting the irrigation tube to the handpiece; and a flexible splash shield slidably mounted to the irrigation tube and having a first position on the tube in which it surrounds at least a portion of the distal end of the irrigation tube and a second position on the tube in which it is proximal to the distal end of the irrigation tube leaving the distal end of the tube uncovered.

15. The tip as defined by claim 14 further including a suction tube substantially coaxially disposed entirely within the irrigation tube.

16. The tip as defined by claim 14 wherein the splash shield is conically shaped and extends distally from a collar to a rim.

17. The tip as defined by claim 14 further including a vent hole formed in the flexible splash shield.

18. The tip as defined by claim 14 wherein the irrigation tube further has a surrounding ridge mounted thereon and a flange attached to the irrigation tube distal of the ridge.

19. The tip as defined by claim 14 wherein the shield is manufactured from a flexible plastic.

20. The tip as defined by claim 14 further including a clip extending proximally from the connector.

21. The tip as defined in claim 10 wherein the irrigation lumen is annular in cross-section.

22. The tip as defined in claim 10 further comprising a plurality of irrigation holes defined at the distal end of the irrigation lumen adapted to emit irrigation fluid in a defined pattern.

23. A tip as defined in claim 10 further comprising:

a nozzle at the distal end of the tip, the nozzle mechanically connecting the irrigation and suction tubes, the central portion of the nozzle having a central suction hole defining the distal end of the suction lumen and a plurality of irrigation holes in communication with the irrigation lumen and disposed circumferentially about the central suction hole.

24. The tip as defined in claim 10 further comprising, in combination, a pump for pressurizing the irrigation liquid, the irrigation tube and irrigation lumen defined therethrough being dimensioned and configured with respect to the pump so that the irrigation fluid is emitted from the tip at a force not exceeding 15 p.s.i.

* * * * *